US012653947B2

(12) United States Patent
Barraud et al.

(10) Patent No.: US 12,653,947 B2
(45) Date of Patent: Jun. 16, 2026

(54) PATCH PUMP DEVICE FOR DRUG DELIVERY

(71) Applicant: Tandem Diabetes Care Switzerland Sàrl, St-Sulpice (CH)

(72) Inventors: Antoine Barraud, Lonay (CH); Benjamin Pruijs, Bienne (CH); Nathanael Sigg, Oulens-sous-Echallens (CH)

(73) Assignee: Tandem Diabetes Care Switzerland Sarl, St-Sulpice (CH)

( * ) Notice: Subject to any disclaimer, the term of this patent is extended or adjusted under 35 U.S.C. 154(b) by 188 days.

(21) Appl. No.: 18/506,136

(22) Filed: Nov. 10, 2023

(65) Prior Publication Data

US 2024/0100248 A1     Mar. 28, 2024

Related U.S. Application Data

(63) Continuation of application No. 18/068,255, filed on Dec. 19, 2022, now Pat. No. 11,813,428, which is a
(Continued)

(30) Foreign Application Priority Data

Dec. 8, 2017     (EP) ...................................... 17206304
Feb. 16, 2018     (EP) ...................................... 18157285

(51) Int. Cl.
| | |
|---|---|
| *A61M 5/142* | (2006.01) |
| *A61M 5/145* | (2006.01) |
| *A61M 5/168* | (2006.01) |

(52) U.S. Cl.
CPC ...... *A61M 5/14248* (2013.01); *A61M 5/1452* (2013.01); *A61M 5/16809* (2013.01);
(Continued)

(58) Field of Classification Search
CPC ............ A61M 5/14248; A61M 5/1452; A61M 5/16809; A61M 2005/14268;
(Continued)

(56) References Cited

U.S. PATENT DOCUMENTS

| | | |
|---|---|---|
| 2,105,200 A | 1/1938 | Phelps |
| 2,412,397 A | 12/1946 | Harper |

(Continued)

FOREIGN PATENT DOCUMENTS

| | | |
|---|---|---|
| CA | 2987866 A1 | 3/2012 |
| DE | 102013111800 A1 | 4/2015 |

(Continued)

OTHER PUBLICATIONS

U.S. Appl. No. 15/777,284 / U.S. Pat. No. 11,806,502, filed May 18, 2018 / Nov. 7, 2023.

(Continued)

*Primary Examiner* — James D Ponton
(74) *Attorney, Agent, or Firm* — Merchant & Gould P.C.

(57) ABSTRACT

A drug delivery device comprising a pumping system (4) and a liquid reservoir (7) fluidly connected to a delivery system outlet (12), the liquid reservoir comprising an elastic plunger (14) scalingly slidable within a container wall (13) of the liquid reservoir for expelling liquid out of the reservoir. The pumping system comprises a piston pump (5) comprising a plunger actuator arranged to displace the plunger (14), and a dosing unit (6) arranged downstream of the liquid reservoir (7) and fluidly connected to the liquid reservoir. The dosing unit (6) comprises a chamber portion (22) arranged between an inlet valve (24) and an outlet valve (26), the chamber portion (22) arranged to receive from the liquid reservoir a pump cycle volume of liquid under an operational pressure greater than ambient pressure generated by the piston pump, and to the deliver said pump cycle
(Continued)

volume of liquid to the delivery system outlet, said pump cycle volume being dependent on the operational pressure.

16 Claims, 9 Drawing Sheets

Related U.S. Application Data continuation of application No. 16/769,566, filed as application No. PCT/EP2018/084069 on Dec. 8, 2018, now Pat. No. 11,529,458.

(52) U.S. Cl.
CPC ............. *A61M 2005/14268* (2013.01); *A61M 2205/0216* (2013.01); *A61M 2205/10* (2013.01); *A61M 2205/3331* (2013.01)

(58) Field of Classification Search
CPC ...... A61M 2205/0216; A61M 2205/10; A61M 2205/3331; A61M 5/14228; A61M 2005/31518
See application file for complete search history.

(56) References Cited

U.S. PATENT DOCUMENTS

| | | | |
|---|---|---|---|
| 3,609,069 A | 9/1971 | Martinelli | |
| 4,042,153 A | 8/1977 | Callahan et al. | |
| 4,199,307 A | 4/1980 | Jassawalla | |
| 4,218,416 A | 8/1980 | Gokcen | |
| 4,236,880 A | 12/1980 | Archibald | |
| 4,273,121 A | 6/1981 | Jassawalla | |
| 4,290,346 A | 9/1981 | Bujan | |
| 4,322,201 A | 3/1982 | Archibald | |
| 4,410,322 A | 10/1983 | Archibald | |
| 4,482,347 A | 11/1984 | Borsanyi | |
| 4,493,704 A | 1/1985 | Beard et al. | |
| 4,498,843 A | 2/1985 | Schneider et al. | |
| 4,501,405 A | 2/1985 | Usry | |
| 4,596,575 A | 6/1986 | Rosenberg et al. | |
| 4,616,802 A | 10/1986 | Tseng et al. | |
| 4,617,014 A | 10/1986 | Cannon et al. | |
| 4,657,490 A | 4/1987 | Abbott | |
| 4,854,836 A | 8/1989 | Borsanyi | |
| 4,934,372 A | 6/1990 | Corenman et al. | |
| 5,056,992 A | 10/1991 | Simons et al. | |
| 5,066,278 A | 11/1991 | Hirschberg et al. | |
| 5,088,522 A | 2/1992 | Rath et al. | |
| 5,137,023 A | 8/1992 | Mendelson et al. | |
| 5,217,355 A | 6/1993 | Hyman et al. | |
| 5,252,044 A | 10/1993 | Raines et al. | |
| 5,318,546 A | 6/1994 | Bierman | |
| 5,482,446 A | 1/1996 | Williamson et al. | |
| 5,637,095 A | 6/1997 | Nason et al. | |
| 5,851,197 A | 12/1998 | Marano et al. | |
| 5,964,583 A | 10/1999 | Danby | |
| 6,093,172 A | 7/2000 | Funderburk et al. | |
| 6,165,151 A | 12/2000 | Weiner | |
| 6,293,925 B1 | 9/2001 | Safabash et al. | |
| 6,607,509 B2 | 8/2003 | Bobroff et al. | |
| 6,723,077 B2 | 4/2004 | Pickup et al. | |
| 6,801,420 B2 | 10/2004 | Talbot et al. | |
| 6,830,562 B2 | 12/2004 | Mogensen et al. | |
| 6,881,043 B2 | 4/2005 | Barak | |
| 7,137,964 B2 | 11/2006 | Flaherty | |
| 7,204,823 B2 | 4/2007 | Estes et al. | |
| 7,315,753 B2 | 1/2008 | Baker, Jr. et al. | |
| 7,329,239 B2 | 2/2008 | Safabash et al. | |
| 7,356,364 B1 | 4/2008 | Bullock et al. | |
| 7,879,023 B2 | 2/2011 | Wood, Jr. | |
| 7,879,026 B2 | 2/2011 | Estes et al. | |
| 8,152,771 B2 | 4/2012 | Mogensen et al. | |
| 8,377,002 B2 | 2/2013 | Hanson et al. | |
| 8,657,807 B2 | 2/2014 | Blomquist | |

| | | | | |
|---|---|---|---|---|
| 9,114,208 B2 | 8/2015 | Smith et al. | | |
| 9,517,024 B2 | 12/2016 | Kiani et al. | | |
| 9,610,018 B2 | 4/2017 | Gulati et al. | | |
| 9,615,779 B2 | 4/2017 | Pryor et al. | | |
| 9,636,457 B2 | 5/2017 | Newberry et al. | | |
| 9,735,502 B2 | 8/2017 | Stevens et al. | | |
| 9,735,893 B1 | 8/2017 | Aleksov et al. | | |
| 9,820,691 B2 | 11/2017 | Kiani | | |
| 9,833,152 B2 | 12/2017 | Kiani et al. | | |
| 9,931,065 B2 | 4/2018 | Pryor et al. | | |
| 9,967,040 B2 | 5/2018 | Aleksov et al. | | |
| 9,980,140 B1 | 5/2018 | Spencer et al. | | |
| 9,993,595 B2 | 6/2018 | Michaud et al. | | |
| 10,137,245 B2 | 11/2018 | Melker et al. | | |
| 10,278,732 B2 | 5/2019 | Schoonmaker et al. | | |
| 10,279,106 B1 | 5/2019 | Cook et al. | | |
| 10,398,320 B2 | 9/2019 | Kiani et al. | | |
| 10,518,069 B2 | 12/2019 | Boden, Jr. et al. | | |
| 11,139,754 B1 | 10/2021 | Shi et al. | | |
| 11,241,530 B1 | 2/2022 | Fridez et al. | | |
| 11,529,460 B1 | 12/2022 | Pruijs et al. | | |
| 11,813,428 B2 * | 11/2023 | Barraud ........... | A61M 5/16809 |
| 2002/0001530 A1 | 1/2002 | Doi et al. | | |
| 2002/0071225 A1 | 6/2002 | Sheldon et al. | | |
| 2002/0091358 A1 | 7/2002 | Klitmose | | |
| 2002/0169439 A1 | 11/2002 | Flaherty | | |
| 2004/0064088 A1 | 4/2004 | Gorman et al. | | |
| 2004/0082920 A1 | 4/2004 | Mori et al. | | |
| 2004/0092873 A1 | 5/2004 | Moberg | | |
| 2004/0158207 A1 | 8/2004 | Hunn et al. | | |
| 2005/0043687 A1 | 2/2005 | Mogensen et al. | | |
| 2005/0101912 A1 | 5/2005 | Faust et al. | | |
| 2005/0124936 A1 | 6/2005 | Mogensen et al. | | |
| 2005/0277887 A1 | 12/2005 | Douglas et al. | | |
| 2006/0036214 A1 | 2/2006 | Mogensen et al. | | |
| 2006/0253086 A1 * | 11/2006 | Moberg ................ | A61M 5/158 |
| | | | 604/272 |
| 2007/0060874 A1 | 3/2007 | Nesbitt et al. | | |
| 2007/0191772 A1 | 8/2007 | Wojcik | | |
| 2007/0191773 A1 | 8/2007 | Wojcik | | |
| 2007/0219496 A1 | 9/2007 | Kamen et al. | | |
| 2008/0051727 A1 | 2/2008 | Moberg et al. | | |
| 2008/0091175 A1 | 4/2008 | Frikart et al. | | |
| 2008/0097289 A1 | 4/2008 | Steil et al. | | |
| 2008/0281290 A1 | 11/2008 | Yodfat et al. | | |
| 2008/0319414 A1 | 12/2008 | Yodfat et al. | | |
| 2009/0069750 A1 | 3/2009 | Schraga | | |
| 2009/0118667 A1 | 5/2009 | Haueter et al. | | |
| 2009/0177146 A1 | 7/2009 | Nesbitt et al. | | |
| 2010/0004598 A1 | 1/2010 | Eberhart et al. | | |
| 2010/0017141 A1 | 1/2010 | Campbell et al. | | |
| 2010/0064236 A1 | 3/2010 | Buck et al. | | |
| 2010/0064257 A1 | 3/2010 | Buck et al. | | |
| 2010/0077198 A1 | 3/2010 | Buck et al. | | |
| 2010/0082167 A1 | 4/2010 | Haueter et al. | | |
| 2010/0106082 A1 | 4/2010 | Zhou | | |
| 2010/0174239 A1 | 7/2010 | Yodfat et al. | | |
| 2010/0211011 A1 | 8/2010 | Haar | | |
| 2010/0228226 A1 | 9/2010 | Nielsen | | |
| 2011/0054439 A1 | 3/2011 | Yodfat et al. | | |
| 2011/0137297 A1 | 6/2011 | Kiani et al. | | |
| 2011/0152769 A1 | 6/2011 | Ramey et al. | | |
| 2011/0152770 A1 | 6/2011 | DiPerna et al. | | |
| 2011/0160652 A1 | 6/2011 | Yodfat et al. | | |
| 2011/0218495 A1 | 9/2011 | Remde | | |
| 2011/0247397 A1 | 10/2011 | Friedli et al. | | |
| 2011/0266999 A1 | 11/2011 | Yodfat et al. | | |
| 2012/0051946 A1 | 3/2012 | Lee et al. | | |
| 2012/0059348 A1 | 3/2012 | Haueter et al. | | |
| 2012/0078181 A1 | 3/2012 | Smith et al. | | |
| 2012/0093311 A1 | 4/2012 | Nierzwick et al. | | |
| 2012/0093315 A1 | 4/2012 | Nierzwick et al. | | |
| 2012/0095393 A1 | 4/2012 | Reinke et al. | | |
| 2012/0150144 A1 | 6/2012 | Campbell et al. | | |
| 2012/0157655 A1 | 6/2012 | Yoneda et al. | | |
| 2012/0209187 A1 | 8/2012 | Kamen et al. | | |
| 2012/0220939 A1 | 8/2012 | Yodfat et al. | | |
| 2012/0226124 A1 | 9/2012 | Blomquist | | |
| 2012/0232485 A1 | 9/2012 | Blomquist | | |

(56) References Cited

U.S. PATENT DOCUMENTS

| 2012/0232486 A1 | 9/2012 | Blomquist |
| 2012/0232521 A1 | 9/2012 | Blomquist |
| 2012/0239362 A1 | 9/2012 | Blomquist |
| 2012/0259185 A1 | 10/2012 | Yodfat et al. |
| 2012/0302991 A1 | 11/2012 | Blomquist et al. |
| 2013/0041342 A1 | 2/2013 | Bernini et al. |
| 2013/0060105 A1 | 3/2013 | Shah et al. |
| 2013/0079709 A1 | 3/2013 | Eberhart et al. |
| 2013/0245555 A1 | 9/2013 | Dirac et al. |
| 2013/0267811 A1 | 10/2013 | Pryor et al. |
| 2013/0338594 A1 | 12/2013 | Da Ros et al. |
| 2014/0128839 A1 | 5/2014 | DiIanni et al. |
| 2014/0148762 A1 | 5/2014 | Haueter et al. |
| 2014/0188516 A1 | 7/2014 | Kamen et al. |
| 2014/0249500 A1 | 9/2014 | Estes |
| 2014/0276419 A1 | 9/2014 | Rosinko et al. |
| 2014/0276420 A1 | 9/2014 | Rosinko |
| 2014/0276574 A1 | 9/2014 | Saint |
| 2014/0288399 A1 | 9/2014 | Regittnig |
| 2014/0378898 A1 | 12/2014 | Rosinko |
| 2015/0073337 A1 | 3/2015 | Saint et al. |
| 2015/0182689 A1 | 7/2015 | Dhami |
| 2015/0182695 A1 | 7/2015 | Rosinko |
| 2015/0182697 A1 | 7/2015 | Panzer |
| 2015/0222517 A1 | 8/2015 | McLaughlin et al. |
| 2015/0265768 A1 | 9/2015 | Vazquez et al. |
| 2016/0008539 A1 | 1/2016 | Miyazaki |
| 2016/0030669 A1 | 2/2016 | Harris et al. |
| 2016/0067403 A1 | 3/2016 | Moberg et al. |
| 2016/0106910 A1 | 4/2016 | Yap et al. |
| 2016/0228641 A1 | 8/2016 | Gescheit et al. |
| 2016/0243302 A1 | 8/2016 | Gyrn |
| 2016/0254952 A1 | 9/2016 | Harvey et al. |
| 2016/0296715 A1 | 10/2016 | Clemenz et al. |
| 2016/0303333 A1 | 10/2016 | Momose |
| 2016/0339172 A1 | 11/2016 | Michaud et al. |
| 2017/0014572 A1 | 1/2017 | Newberry et al. |
| 2017/0027523 A1 | 2/2017 | Venkatraman et al. |
| 2017/0056582 A1 | 3/2017 | Niklaus |
| 2017/0072140 A1 | 3/2017 | Bazargan et al. |
| 2017/0112534 A1 | 4/2017 | Schoonmaker et al. |
| 2017/0188911 A1 | 7/2017 | Halac et al. |
| 2017/0238805 A1 | 8/2017 | Addison et al. |
| 2017/0259015 A1 | 9/2017 | Caspers |
| 2017/0274146 A1 | 9/2017 | Newberry et al. |
| 2017/0368258 A1 | 12/2017 | Fleischer |
| 2018/0000999 A1 | 1/2018 | Dolmatch et al. |
| 2018/0025120 A1 | 1/2018 | Cronrath et al. |
| 2018/0060520 A1 | 3/2018 | Degen et al. |
| 2018/0207356 A1 | 7/2018 | Joseph et al. |
| 2018/0256813 A1 | 9/2018 | Chow et al. |
| 2018/0280608 A1 | 10/2018 | Gillett et al. |
| 2018/0318550 A1 | 11/2018 | Chiu et al. |
| 2018/0333532 A1 | 11/2018 | Wei |
| 2018/0339102 A1 | 11/2018 | Barraud et al. |
| 2019/0001055 A1 | 1/2019 | Gyrn |
| 2019/0083712 A1 | 3/2019 | List |
| 2019/0091404 A1 | 3/2019 | Nazzaro et al. |
| 2019/0133505 A1 | 5/2019 | Jager |
| 2019/0151568 A1 | 5/2019 | Cardinali et al. |
| 2019/0160225 A1 | 5/2019 | Verlaak et al. |
| 2019/0175818 A1 | 6/2019 | Meenken |
| 2019/0184072 A1 | 6/2019 | Madden et al. |
| 2019/0192768 A1 | 6/2019 | Gupta et al. |
| 2019/0255251 A1 | 8/2019 | Diianni et al. |
| 2019/0351134 A1 | 11/2019 | Cook et al. |
| 2020/0016335 A1 | 1/2020 | DiPerna et al. |
| 2020/0023122 A1 | 1/2020 | McCullough et al. |
| 2020/0037891 A1 | 2/2020 | Kiani et al. |
| 2020/0069875 A1 | 3/2020 | Nazzaro et al. |
| 2020/0101219 A1 | 4/2020 | Wang et al. |
| 2020/0329433 A1 | 10/2020 | Kruse et al. |
| 2020/0360235 A1 | 11/2020 | Møller |
| 2020/0373009 A1 | 11/2020 | Shapley et al. |
| 2021/0038813 A1 | 2/2021 | O'Connor et al. |
| 2021/0093779 A1 | 4/2021 | Trachtenberg |
| 2021/0162119 A1 | 6/2021 | Barraud et al. |
| 2021/0213198 A1 | 7/2021 | Gyory |
| 2021/0272687 A1 | 9/2021 | Klopfenstein et al. |
| 2021/0280309 A1 | 9/2021 | Klopfenstein et al. |
| 2022/0226568 A1 | 7/2022 | Oberg et al. |

FOREIGN PATENT DOCUMENTS

| EP | 0721358 A1 | 7/1996 |
| EP | 1410814 A2 | 4/2004 |
| EP | 1716879 A1 | 11/2006 |
| EP | 1944150 A1 | 7/2008 |
| EP | 2436414 A2 | 4/2012 |
| EP | 2698178 A2 | 2/2014 |
| EP | 2852122 A1 | 3/2015 |
| GB | 2065789 A | 7/1981 |
| WO | WO-8001934 A1 | 9/1980 |
| WO | WO-0220073 A2 | 3/2002 |
| WO | WO-2005016534 A1 | 2/2005 |
| WO | WO-2008155377 A1 | 12/2008 |
| WO | WO-2016196587 A1 | 12/2016 |
| WO | WO-2017085624 A1 | 5/2017 |
| WO | WO-2017205816 A1 | 11/2017 |
| WO | WO-2019110839 A1 | 6/2019 |
| WO | WO-2022107078 A1 | 5/2022 |

OTHER PUBLICATIONS

U.S. Appl. No. 16/769,566 / U.S. Pat. No. 11,529,458, filed Jun. 3, 2020 / Dec. 20, 2022.

U.S. Appl. No. 17/102,334 / U.S. Pat. No. 11,241,530, filed Nov. 23, 2020 / Feb. 8, 2022.

U.S. Appl. No. 17/257,733, filed Jan. 4, 2021.

U.S. Appl. No. 17/257,775, filed Jan. 4, 2021.

U.S. Appl. No. 17/652,448 / U.S. Pat. No. 11,529,460, filed Feb. 24, 2022 / Dec. 20, 2022.

U.S. Appl. No. 17/652,453 / U.S. Pat. No. 11,529,461, filed Feb. 24, 2022 / Dec. 20, 2022.

U.S. Appl. No. 17/652,456 / U.S. Pat. No. 11,529,464, filed Feb. 24, 2022 / Dec. 20, 2022.

U.S. Appl. No. 17/652,460 / U.S. Pat. No. 11,541,169, filed Feb. 24, 2022 / Jan. 3, 2023.

U.S. Appl. No. 17/652,463 / U.S. Pat. No. 11,712,514, filed Feb. 24, 2022 / Aug. 1, 2023.

U.S. Appl. No. 18/058,041 / U.S. Pat. No. 11,679,199, filed Nov. 22, 2022 / Jun. 20, 2023.

U.S. Appl. No. 18/058,003, filed Nov. 22, 2022.

U.S. Appl. No. 18/058,074, filed Nov. 22, 2022.

U.S. Appl. No. 18/058,088 / U.S. Pat. No. 11,813,382, filed Nov. 22, 2022 / Nov. 14, 2023.

U.S. Appl. No. 18/068,255 / U.S. Pat. No. 11,813,428, filed Dec. 19, 2022 / Nov. 14, 2023.

U.S. Appl. No. 18/253,854, filed May 22, 2023.

U.S. Appl. No. 18/335,938, filed Jun. 15, 2023.

U.S. Appl. No. 18/360,758, filed Jul. 27, 2023.

U.S. Appl. No. 18/502,928, filed Nov. 6, 2023.

Accu-Check Solo, User's Manual, Accu-Check Solo micropump system, Roche Diabetes Care (2019).

Camara et al., Security and Privacy Issues in Implantable Medical Devices: A Comprehensive Survey, Journal of Biomedical Informatics, 55:272-289 (Jun. 2015).

Ebrahim et al., "New secure healthcare system using cloud of things", Cluster Computing, vol. 20, No. 3, May 5, 2017, pp. 2211-2229.

Fomichev et al., "Survey and Systematization of Secure Device Pairing", ARXIV.org, Cornell University Library, Sep. 8, 2017.

International Search Report & Written Opinion dated Feb. 23, 2022 in Int'l PCT Patent Appl. Serial No. PCT/IB2021/060766 (0510).

International Search Report & Written Opinion dated Oct. 4, 2022 in Int'l PCT Patent Appl. Serial No. PCT/IB2022/054863 (0610).

International Search Report and Written Opinion of the ISA for PCT/IB2016/056870, mailed Feb. 3, 2017, 11 pages.

(56)         References Cited

OTHER PUBLICATIONS

International Search Report for PCT/EP2018/084069, mailed Apr. 8, 2019, 7 pages (0210 PCT).
International Search Report for PCT/EP2019/068053, mailed Sep. 19, 2019, 4 pages (0310 PCT).
International Search Report for PCT/EP2019/068054, mailed Sep. 19, 2019, 4 pages (0410 PCT).
Lewotsky, Kristin, Tutorial: The Basics of Stepper Motors—Part I, Association for Advancing Automation (Feb. 12, 2014).
Medtronic MiniMed (tm) 770G, System User Guide, https://www.medtronicdiabetes.com/sites/default/files/library/download-library/user-guides/MiniMed_770G_System_User_Guide.pdf (2020).
Omnipod-Insulin Management System, UST400 User Guide, https://www.omnipo.com/sites/default/files/2021-04/Omnipod-System_User-Guide_English (Apr. 2021).
Osram—Light is Wearable, Health Monitoring and Fitness Tracking, Osram Opto Semiconductors, Flyer posted online Jan. 22, 2015, (Year: 2015).
Park, "Security Mechanism Based on Hospital Authentication Server for Secure Application of Implantable Medical Devices", Biomed Research International, vol. 2014, Jul. 24, 2014, pp. 1-12.
T:slim Insulin Pump, User Guide, Tandem Diabetes Care, https://www.tandemdiabetes.com/docs/default-source/product-documents/tslim-insulin-pump (2017).
Written Opinion of the ISA for PCT/EP2018/084069, mailed Apr. 8, 2019, 9 pages (0210 PCT).
Written Opinion of the ISA for PCT/EP2019/068053, mailed Sep. 19, 2019, 7 pages (0310 PCT).
Written Opinion of the ISA for PCT/EP2019/068054, mailed Sep. 19, 2019, 9 pages (0410 PCT).
Wu et al., "A Secure Proxy-based Access Control Scheme for Implantable Medical Devices", ARXIV.org, Cornell University Library, Mar. 21, 2018.

* cited by examiner

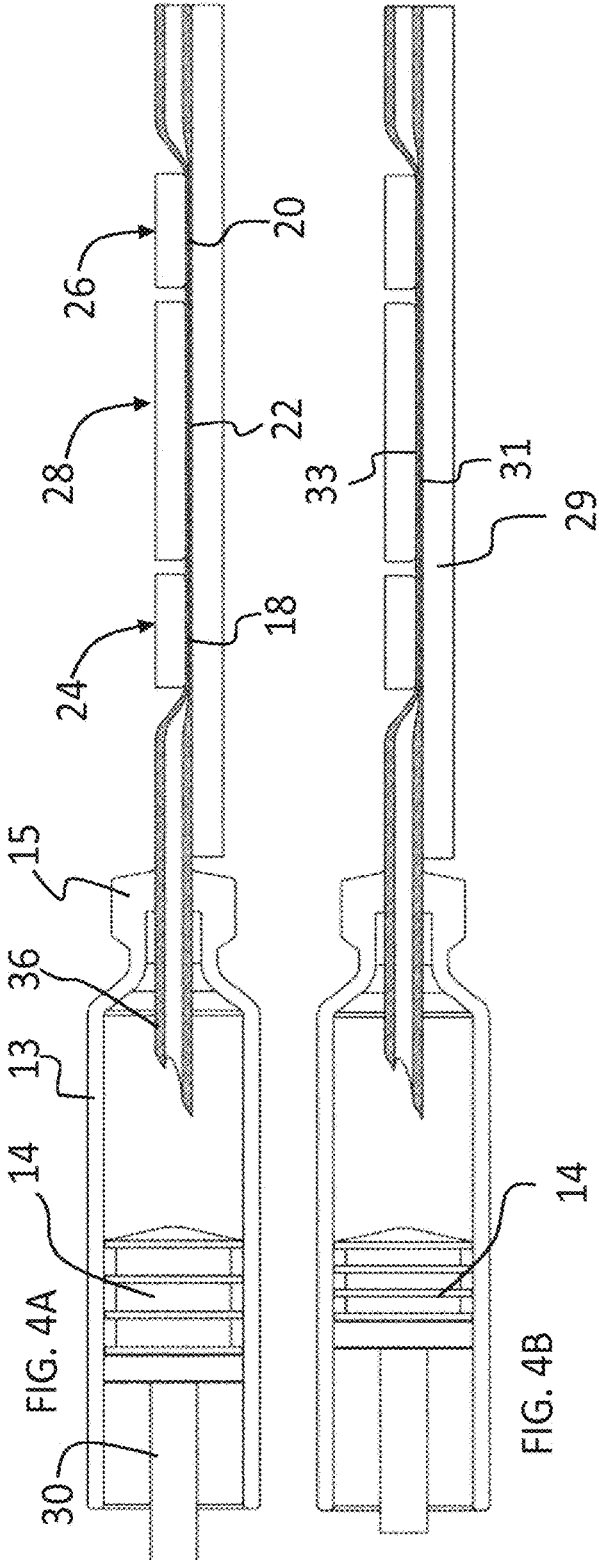
FIG. 4A
FIG. 4B
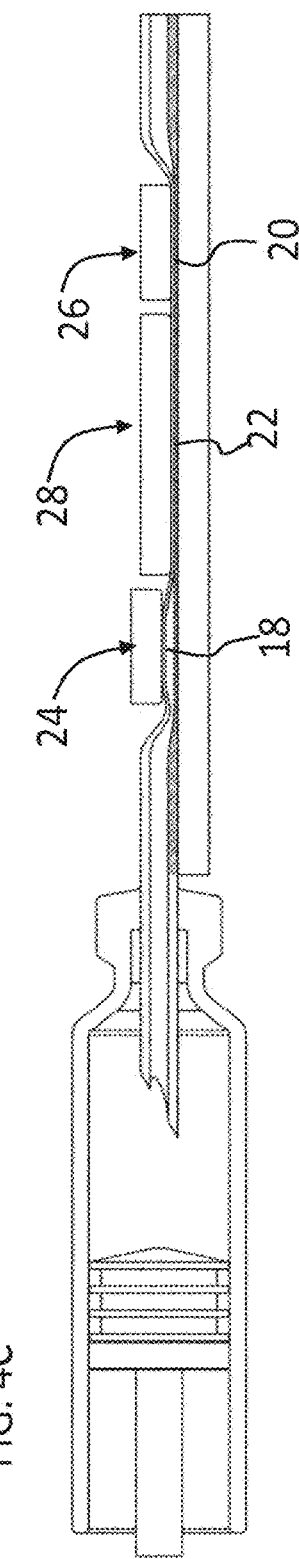
FIG. 4C

PATCH PUMP DEVICE FOR DRUG DELIVERY

CROSS-REFERENCE TO RELATED APPLICATIONS

This application is a continuation of U.S. patent application Ser. No. 18/068,255, filed Dec. 19, 2022, now U.S. Pat. No. 11,813,428, which is a continuation of U.S. patent application Ser. No. 16/769,566, filed Jun. 3, 2020, now U.S. Pat. No. 11,529,458, which is a U.S. national stage application of PCT/EP2018/084069, filed Dec. 8, 2018, which claims priority to EP patent application Ser. No. 18/157,285.0, filed Feb. 16, 2018, and EP patent application Ser. No. 17/206,304.2, filed Dec. 8, 2017, the entire contents of each of which are incorporated herein by reference.

FIELD OF THE INVENTION

This invention relates to a drug delivery device, in particular for the transcutaneous administration of a liquid drug.

BACKGROUND OF THE INVENTION

Various drug delivery devices for transcutaneous administration of a drug are available on the market. Certain drug delivery devices are intended for use as a patch unit to be worn by the patient. Typically, such devices comprise a disposable unit with an adhesive patch that is arranged for temporarily bonding against the skin of a patient, the disposable unit having a needle, or catheter connected to a needle, that is injected through the patient's skin for transcutaneous administration of a liquid medicament. Certain devices comprise a reusable drive unit separably mounted to the disposable unit for reuse with other disposable units, the reusable unit containing an electrical motor drive for pumping the liquid medicament and control electronics. There are many drugs that may be administered using a patch pump unit, one of the most widespread applications being for the injection of insulin to diabetes patients.

It is generally advantageous to provide a drug delivery device that is compact, but this advantage is particularly relevant for patch pump units that are worn by the patient in order to increase comfort to the patient. In order to decrease the size of wearable drug delivery devices, certain drugs are provided in concentrated formulations. For instance insulin may be provided in a concentrated formulation. One of the difficulties associated with the administration of concentrated drugs is however the increased need for dosage accuracy per injection cycle as well as overall in the case of multiple injection cycles, With a drug such as insulin, there may be basal as well as bolus delivery of insulin for instance after a meal.

One of the well-known pump designs used in drug delivery devices are piston pumps. These typically comprise a motor coupled to a linear actuator that pushes a plunger of a cartridge reservoir containing the liquid medicament. The displacement of the linear actuator may be very precise, particularly considering the high reduction between the motor and the linear displacement element, typically driven by a screw coupled to a rotor of the motor. Linear piston pumps are very accurate and reliable over a certain number of pumping cycles, however there may be variations between one pumping cycle and the next. These variations occur due to the compressible nature of the plunger that is driven by the actuator and the stick-slip effect due to friction between the plunger which is typically made of an elastomeric material and the walls of the reservoir. In the case of concentrated medicaments, such variations may not meet the required accuracy taking into account the concentration of the drug. In addition, many existing piston pump mechanisms are too large to provide comfort to the user.

Other drug delivery pumps that do not rely on the advancement of a plunger in a reservoir are known, for instance pumps that draw in liquid from a reservoir where the volume is determined by the flow of liquid through the pump. Such pumps however also have drawbacks, for instance while the variations between pumping cycles may be lower than in a plunger system, the overall accuracy over a certain number of cycles may not be as good as in a plunger pump and the negative suction required to draw the drug may decrease the pumped volume and increase the creation of bubbles in the liquid medicament, which is undesirable. Also, such systems are often used with drug reservoirs in which a medicament has been transferred from a standard cartridge into a dedicated cartridge in the drug delivery device.

In order to reduce risk of false manipulation and increase safety and reliability, where possible, it is preferable to provide a pumping system that does not require a transfer of drug and that can be used with standard cartridges or vials in which the medicament is typically supplied. It is known for instance to provide vials that are equipped with a plunger that can be displaced in order to allow delivery of the medicament out of the vial.

SUMMARY OF THE INVENTION

In view of the foregoing, it is an object of this invention to provide a drug delivery device that is safe and reliable to use, and that is accurate over one cycle as well as accurate over a large number of cycles.

It is advantageous to provide a drug delivery device with a pumping system that minimizes the formation of bubbles in a liquid medicament to be delivered to a patient.

It is advantageous to provide a drug delivery device that is very compact.

It is advantageous to provide a drug delivery device that is economical to produce.

It is advantageous to provide a drug delivery device that may be used with pre-filled drug reservoir cartridges equipped with a plunger.

Disclosed herein is a drug delivery device comprising a pumping system and a liquid reservoir fluidly connected to a delivery system outlet, the liquid reservoir comprising an elastic plunger sealingly slidable within a rigid container wall of the liquid reservoir for expelling liquid out of the reservoir. The pumping system comprises a piston pump comprising an electrically driven plunger actuator arranged to displace the plunger a predefined distance per pump cycle, and a dosing unit arranged downstream of the liquid reservoir and fluidly connected to the liquid reservoir. The dosing unit comprises a chamber portion arranged between an inlet valve and an outlet valve, the chamber portion arranged to receive from the liquid reservoir a discrete pump cycle volume of liquid under an operational pressure generated by the piston pump greater than ambient pressure, and to deliver said discrete pump cycle volume of liquid to the delivery system outlet, said pump cycle volume being dependent on the operational pressure.

This very advantageously allows for an advantageous self-adapting injection volume as the dosing unit varies its displaced volume as a function of the input pressure In an advantageous embodiment, the dosing unit comprises or is in the form of a peristaltic pumping unit.

In an advantageous embodiment, the chamber portion is elastically expandable at least in a state when filled with a pump cycle volume of liquid.

In an advantageous embodiment, an elastic property of the elastic expandable chamber portion defined by a volume change $\Delta V$ multiplied by an operational pressure greater than ambient pressure $\Delta P$ is in a range of: $5 \cdot 10^{-8} < \Delta V \times \Delta P < 1 \cdot 10^{-3}$ [m$^3$ Pa], more preferably in a range of $5 \cdot 10^{6} < \Delta V \times \Delta P < 1 \cdot 10^{-4}$ [m$^3$ Pa].

The operational pressure is in a range between 10 and 1600 millibars over ambient pressure, preferably in a range of 100 to 1000 millibars.

In certain embodiments, the operational pressure may advantageously be in a range of 500 to 1000 millibars.

In an advantageous embodiment, the dosing unit comprises a flexible tube incorporating the chamber portion.

In an embodiment, the chamber portion comprises top and bottom walls that lie against each other when the chamber portion is empty, and that separate apart as the chamber portion is filled with liquid, the bottom wall resting against a base of the dosing unit.

The bottom wall may be bonded to the base along at least portions of the perimeter of the bottom wall or at least portions distributed over the surface of the bottom wall such that when liquid is injected into the chamber portion and the top wall moves away from the bottom wall, an elastic tensile stress is generated in the top wall of the chamber portion.

In an advantageous embodiment, the inlet and outlet valves are in the form of pinch valves.

In an advantageous embodiment, the drug delivery device comprises a pump chamber actuator arranged to bias against the chamber portion to expel liquid out of the chamber portion to deliver said pump cycle volume of liquid to the delivery system outlet.

In embodiments, the pump chamber actuator may be spring biased and/or actively driven by an electrical actuator.

In an advantageous embodiment, the plunger actuator comprises an actuation rod formed of a curved spring sheet beam, the actuation rod being bent around a U-shape.

In an advantageous embodiment, the U-Shape bent portion of the actuation rod is slidably guided in a housing guide slot of the housing.

In an advantageous embodiment, a housing portion forming the housing guide slot in which the actuation rod slides, is made of a polymer.

In an advantageous embodiment, the polymer is Polytetrafluoroethylene (PTFE).

In an advantageous embodiment, the housing guide slot comprises roller bearings mounted along the guide slot on a convex side of the bent section.

In an advantageous embodiment, the housing guide slot is made integrally with the housing of injected polymer.

In an advantageous embodiment, the actuation rod is made of a tape of spring metal.

In an advantageous embodiment, the spring metal is a stainless steel alloy.

In an advantageous embodiment, the plunger actuator comprises a linear actuator and a bent actuation rod coupled at a first end to the linear actuator and at a second end to the plunger, the linear actuator being arranged parallel and laterally adjacent to the liquid reservoir.

In an advantageous embodiment, the linear actuator comprises a linear screw and a nut blocked in rotation and slidably movable upon rotation of the screw.

In an advantageous embodiment, the liquid reservoir, dosing unit, and drug outlet form part of a disposable part of the drug delivery device connectable and separable from a reusable part of the drug delivery device, the reusable part comprising the plunger actuator, a control system for controlling the pump system, and an electrical drive unit coupled to the plunger actuator.

In an advantageous embodiment, the dosing unit is configured such that a minimal number of 100 cycles must be performed for the dosing unit to empty the cartridge.

Also disclosed herein is a method of operating a drug delivery device as set forth above comprising the steps of:
a) operating the plunger actuator to advance the plunger and create an overpressure in the liquid reservoir,
b) opening the inlet valve while the outlet valve and operating the plunger actuator to advance the plunger and fill the chamber portion with a pump cycle volume of liquid thus creating an operational pressure in the chamber portion that is greater than ambient pressure,
c) closing the inlet valve, opening the outlet valve, and emptying the chamber portion by actuation of the pump chamber actuator either passively or actively,
d) closing the outlet valve,
e) optionally repeating steps b) to d),
f) optionally operating first steps b) to d) and then a),
g) optionally operating steps a) and b) to d) simultaneously.

In an advantageous embodiment, the operational pressure is greater or smaller than a target pressure due to a predefined target volume of liquid being filled in the chamber portion, said target volume being considered as the fill volume of the chamber portion at a target pressure without any pressure exerted by a pump chamber actuator.

In certain embodiments the target pressure is ambient pressure, whereby when the chamber portion is filled with a predefined target volume, the chamber walls are not elastically stressed and do not exert per se any compression on the liquid therein. In this embodiment the operational pressure is always greater than said target pressure.

In another embodiment, the chamber portion wall is under elastic tension already from the initial filling of liquid such that at a predefined target volume, the chamber portion wall exerts pressure on the liquid within the chamber portion. In this embodiment, the operational pressure may be situated around the target pressure, either less than the target pressure, or greater than the target pressure.

In an advantageous embodiment, the operational pressure in the chamber portion in step b) is in a range of between 10 and 1600 millibars over ambient pressure, preferably in a range between 100 and 1000 millibars over ambient pressure. In certain embodiments the operational pressure is advantageously in a range between 500 and 1000 millibars over ambient pressure.

In an embodiment where the target pressure is ambient pressure, said pump cycle volume of liquid is in a range of 1% to 50%, preferably in a range of 2% to 30% greater than a predefined the maximum volume of the chamber portion at ambient pressure. This additional volume over the maximum volume is obtained by elastic expansion of the wall of the chamber portion.

It may be noted that in variants the chamber portion may be pressed flat by the pump chamber actuator, for instance by a pre-stressed spring biased pump chamber actuator, such that the volume at ambient pressure inside the chamber is essentially zero due to the pressure exerted by the pump chamber actuator.

Further objects and advantageous aspects of the invention will be apparent from the claims, and from the following detailed description and accompanying figures.

BRIEF DESCRIPTION OF THE DRAWINGS

The invention will now be described with reference to the accompanying drawings, which by way of example illustrate the present invention and in which:

FIGS. 4*a* to 4H illustrate the dosing unit of FIG. 3 in different pumping steps;

DETAILED DESCRIPTION OF EMBODIMENTS OF THE INVENTION

Figures 1, 1A:
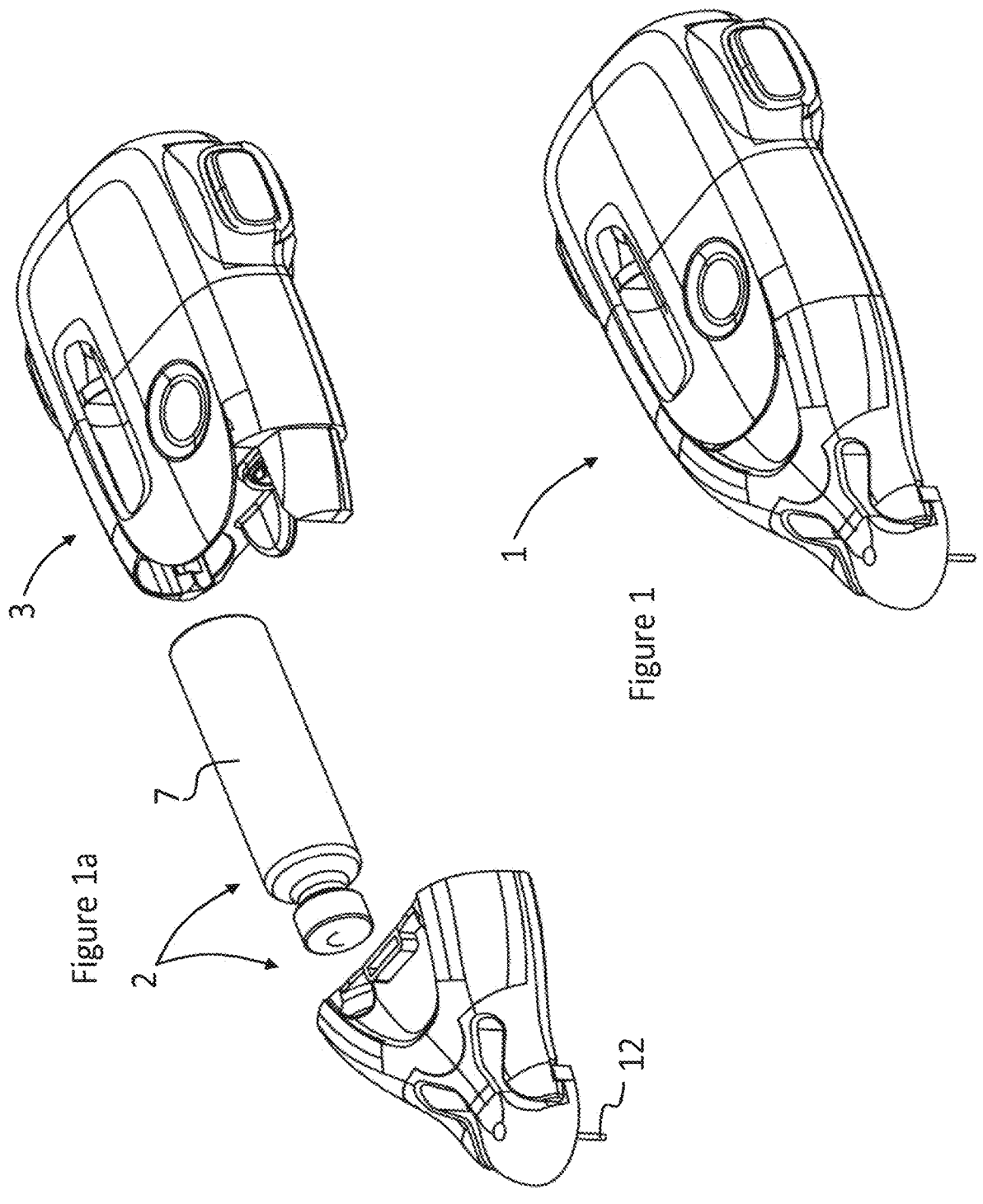
FIG. 1 is a perspective view of a drug delivery device according to embodiments of the invention.
FIG. 1*a* is a perspective view of the drug delivery device of FIG. 1 showing the disposable and reusable parts separated.
Figures 2, 2A:
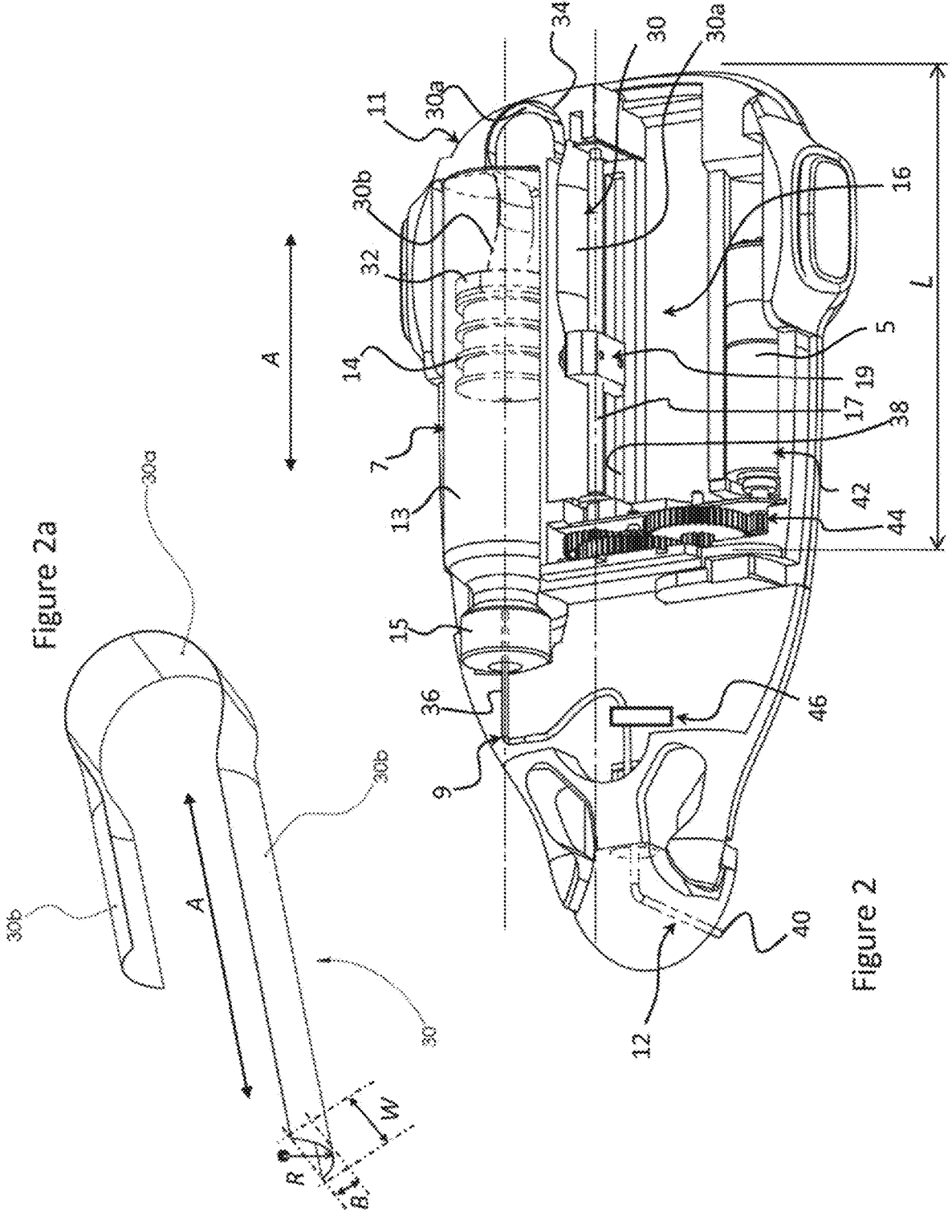
FIG. 2 is a perspective view of a portion of the drug delivery device of FIG. 1, showing in particular a pumping system according to an embodiment of the invention.
FIG. 2*a* is a perspective view illustrating an actuation rod of the pumping system according to an embodiment of the invention.
Figures 3, 3A, 3B:
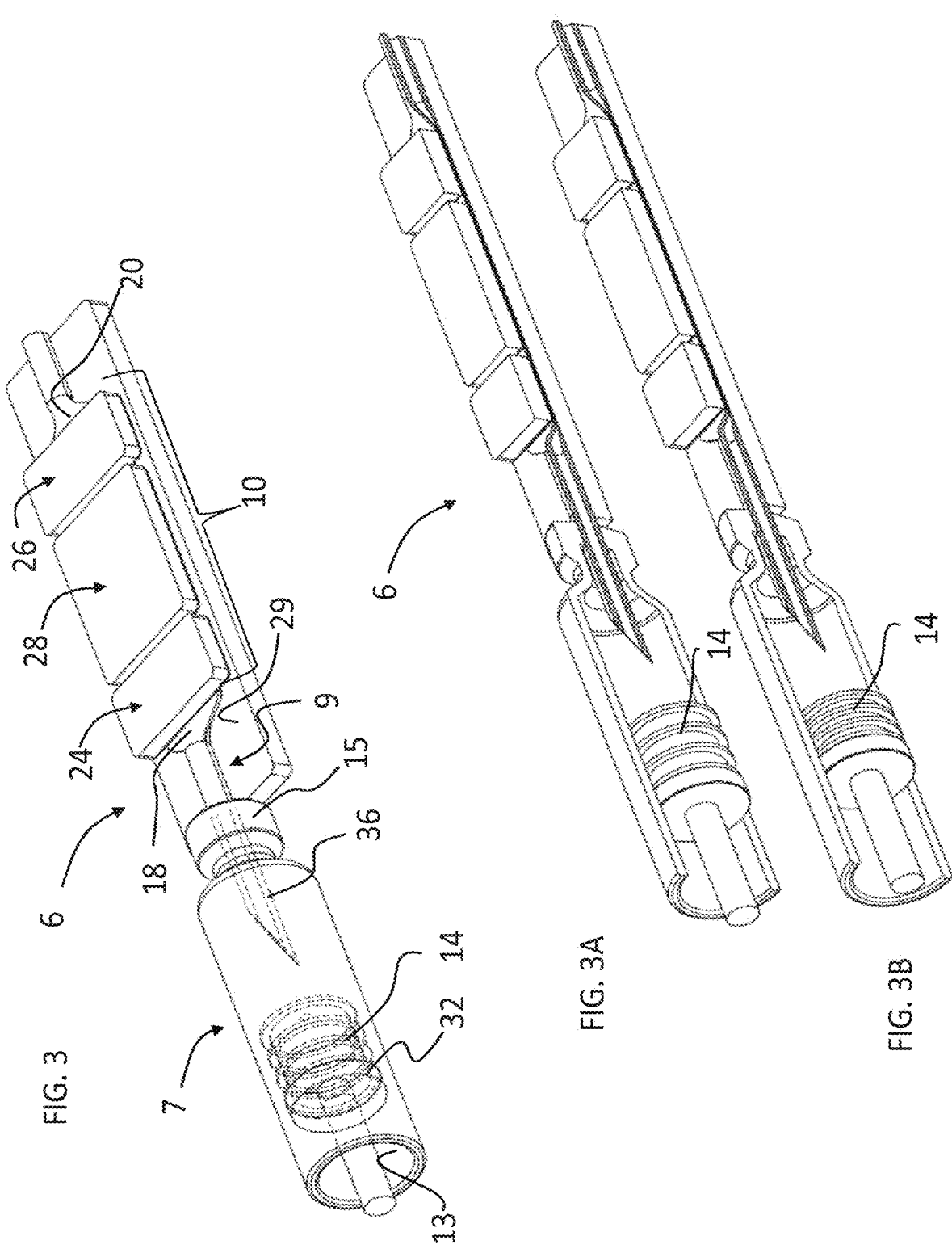
FIG. 3 is a schematic perspective view of a dosing unit of a pumping system according to an embodiment of the invention.
FIG. 3*a* is a cross-sectional view of the dosing unit illustrated in FIG. 3 showing a plunger in an uncompressed state.
FIG. 3*b* is a view similar to FIG. 3*a* showing the plunger in a compressed state and the liquid inside the reservoir at a pressure higher than atmospheric pressure.

Referring to the figures, starting with FIGS. 1 to 3, a drug delivery device 1 according to an embodiment of this invention includes a delivery system outlet 12 comprising a transcutaneous needle or a catheter tube for connection to a transcutaneous needle, a liquid reservoir 7 containing a medicament to be administered to a patient, a pumping system, and an electronic control and power supply system (not shown). The pumping system according to the invention comprises a piston pump 5 acting upon the liquid reservoir 7 and a dosing unit 6 interconnecting the liquid reservoir 7 to the delivery system outlet 12.

The drug delivery device according to an advantageous embodiment may comprise a multi-use reusable portion 2 and a single-use disposable portion 3 separable from the reusable part.

The drug delivery device according to an advantageous embodiment may be in the form of a patch pump device for mounting against the patient's skin with a transcutaneous needle fixed directly to the disposable parts and injectable through the patient's skin.

The drug delivery device according to the invention however includes embodiments that are not in the form of patch units, for example in the form of a portable autonomous device that may be carried by the patient on a belt, in a pocket or bag, or placed on a table and connected for instance via a catheter to the patient. Embodiments may also include a drug delivery device for bolus administration of a medicament that is temporarily placed against a patient's skin at the time of administering the bolus dose and removed from the patient after or between administrations of a dose.

In a patch unit embodiment of the drug delivery device, the disposable part 2 may comprise a housing support with an adhesive base for bonding to the patient's skin. The electronic control and power supply systems (not shown) may advantageously be mounted in the reusable part 2. Further, a drive unit 11 comprising an electrical motor 42 for driving a plunger actuator of the piston pump 5 may be mounted in the reusable part 3. The components mounted in the disposable part may include the liquid reservoir 7, the dosing unit 6, the delivery system outlet 12 and the liquid flow channels fluidly interconnecting the aforesaid components.

In an embodiment, the liquid reservoir 7 comprises a container wall 13, in particular a cylindrical container wall, hermetically sealed at one end by a plunger 14 that is sealingly and slideably movable within the container wall 13 as liquid medicament contained within the liquid reservoir is expelled. The other end of the container wall 13 may be provided with a cap 15 comprising a septum arranged to be pierced by a hollow needle. In variants of the invention, instead of a cap with a septum, other fluidic connection systems such as a cap with a valve or other devices allowing liquid to flow out of the reservoir into a downstream liquid flow channel that are per se known may be provided.

In preferred embodiments, the liquid reservoir 7 including the plunger 14 and cap 15 may be a standard vial of a drug manufacturer assembled in the reusable part 3 or disposable part 2, or a custom reservoir integrated in the disposable part 2 during manufacture of the disposable part.

The piston pump 5 comprises a plunger actuator arranged to push the plunger 14 into the container 13 thus applying pressure on the liquid contained within the reservoir 7. In the illustrated embodiment, the plunger actuator comprises a linear actuator 16 comprising a screw 17 coupled to and driven in rotation by a motor 42 of the drive unit 11, and a nut 19 coupled to the screw 17, the nut 19 being blocked in rotation by a housing linear guide 38 but skiable in an axial direction A corresponding to the axis of rotation A of the screw 17.

In the illustrated embodiment, the screw 17 is advantageously arranged essentially parallel and laterally adjacent to a central axis of the liquid reservoir 7 as defined by the direction of displacement of the plunger 14. An actuation rod 30 interconnects the nut 19 to a piston plate 32 pressing against the plunger 14.

In a preferred embodiment, the actuation rod 30 is a bendable rod comprising a bent section 30*a* forming a U shape between straight sections 30*b*.

The parallel adjacent arrangement of the linear actuator 16 and liquid reservoir 7 allows to provide a particularly compact piston pump and reservoir arrangement, in particular reducing the overall length L of the piston pump arrangement so that it may be conveniently mounted within a patch pump housing in a compact arrangement.

In an advantageous embodiment, the bent actuation rod 30 may comprise a curved profile in an unbent state, when viewed in cross section orthogonal to the plunger displacement direction A.

The actuation rod may be made of a spring sheet metal beam configured to generate an essentially flattened profile in cross-section along a portion of the rod that is bent around a U shape as illustrated in FIG. 2. This configuration allows the actuation rod to be rigid in the direction of a buckling force aligned with the linear sections 30*b*, yet flexible in a transverse direction to allow bending into the U shaped bent portion 30*b* such that a force may be transmitted by the nut 19 in the plunger displacement direction A to the rod 30, the force being transmitted in the rod around the U-bend to the piston plate 32.

The bent portion 30*a* may be guided in a housing guide slot 34 in a housing portion of the pumping system.

The housing portion forming the housing guide slot 34 may advantageously be made of a low friction polymer such as Polytetrafluoroethylene (FIFE) to guide the flattened profile bent portion 30*a* of the actuation rod 30 as it slides in the slot 34 when the nut 19 is advanced or retracted by rotation of the screw 17.

Other low friction guide mechanisms may be provided in variants, for instance comprising roller bearings mounted along the guide slot on a convex side of the bent section 30*a*.

The actuation rod 30 may advantageously be made of a tape of spring metal such as a stainless steel alloy.

In an advantageous embodiment of a drug delivery device, the tape of spring metal may have the following parameters:

Tape metal thickness h between 40 and 60 micrometres $(10^{-6}$ m)

Width w between 5 and 12 mm

Bending height B between 0.5 and 2 mm

Radius R between 4 and 10 mm

The drive unit 11 may be actuated in a reverse direction to retract the nut 19 from the fully extended position P1 to the fully retracted position P2 to allow the liquid reservoir 7 and disposable part 2 of the drug delivery device to be disconnected and separated from the reusable part 3 of the drug delivery device and for coupling a new disposable part to the reusable part. Once the disposable part has been coupled to the reusable part, the piston plate 32 may be advanced until it abuts the rear end of the plunger 14 invention.

The drive unit 11 may comprise an electrical motor 42 connected to a reduction gear system 44 driving the screw 17 at a reduced rate of rotation speed compared to the rotor of the motor. The electrical motor may include a reduction system within the motor housing. The reduction gear system may also be formed of a first stage gearbox within the motor and a second stage gearbox outside of the motor, coupled to an output of the motor as illustrated in FIG. 2 for instance. Such linear actuators are per se known in the art and need not be described in further detail. It may be noted however that the linear actuator 16 may comprise other configurations per se known in the field of linear actuators, connected to the bent actuation rod 30.

The cap 15 of the liquid reservoir 7 is fluidly connected to the dosing unit 6. In the illustrated embodiment, the dosing unit comprises a hollow needle 36 that pierces through a septum of the cap 15. The hollow needle 36 is connected to a liquid conduit 9 of the dosing unit 6. The liquid conduit 9 comprises an inlet portion 18, an outlet portion 20, and therebetween a chamber portion 22. The dosing unit further comprises an actuation system 10 comprising an inlet valve 24 acting upon the inlet portion 18, an outlet valve 26 acting upon the outlet portion 20, and a pump chamber actuator 28 acting upon the chamber portion 22 of the liquid conduit.

In an advantageous embodiment, the liquid conduit may be formed of a flexible tube 9, for instance a tube made of a plastic material.

The dosing unit further comprises a base 29 on which the chamber portion is mounted. The pump chamber actuator 28 may be configured to bias upon the chamber portion towards the base 29, thereby pressing the chamber portion 22 against the base 29. The valves 24, 26 may also be configured to bias upon the inlet and outlet portions respectively, thereby pressing them against the base 29.

Figure 4D:
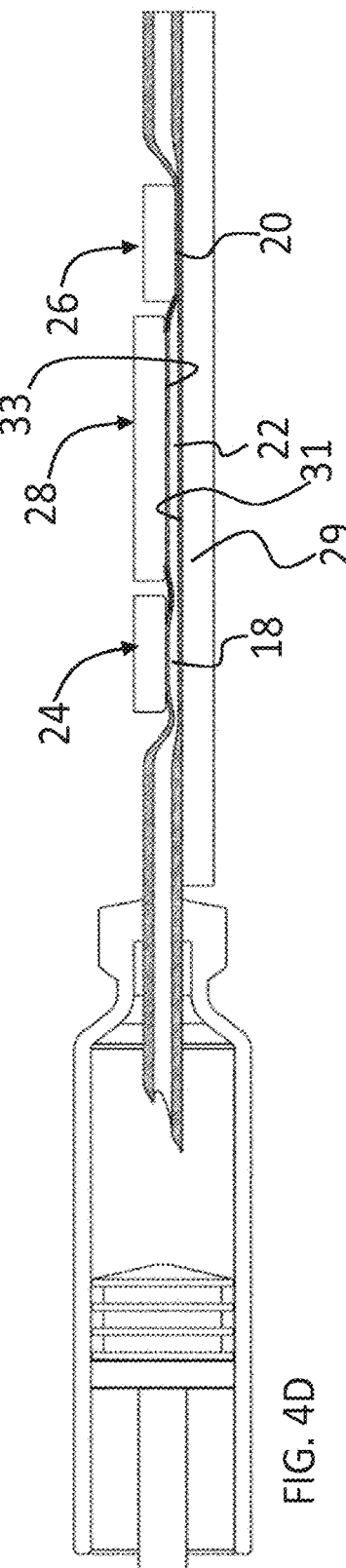

In an embodiment, the chamber portion 22 may comprise top and bottom walls 33, 31 that may be in an essentially flat planar form lying against each other when the chamber portion is empty, for instance as illustrated in FIG. 4*b*, and that separate apart as the chamber portion is filled with liquid, for instance as illustrated in FIG. 4*d*. The bottom wall may rest against a base 29 of the dosing unit. In an embodiment, the bottom wall may be bonded, for instance by welding or adhesive, to the base 29.

In an embodiment the bottom wall 31 may be bonded to the base 29 in an arrangement configured such that when liquid is injected into the chamber portion and the top wall 33 moves away from the bottom wall 31, an elastic tensile stress is generated in the top wall 33 of the chamber portion. This elastic tension in the top wall 33 of the chamber portion 22 exerts a pressure on the liquid contained within the chamber portion. The bottom wall 31 is this embodiment may be bonded to the base 29 along its outer perimeter, or along portions of the outer perimeter, for instance along opposed lateral edges of the bottom wall. The bottom wall, in variants may also be bonded to the base 29 over essentially the whole surface of the bottom wall 31 or at discrete spots or portions distributed over the bottom wall. Any bonding configuration may be employed that serves the purpose of keeping the bottom wall bonded to the base as the top wall is being tensioned by the liquid filling the chamber portion 22.

The inlet valve, outlet valve and pump chamber actuator 24, 26, 28 may be actuated independently of each other and are configured to move between a position where the fluid channel inside the tube is closed, thus preventing flow of liquid through the tube, to an open state in which the channel in the tube is open allowing through-flow of liquid.

In an advantageous embodiment, in which the liquid conduit 9 comprises a flexible tube, the inlet and outlet valves 24, 26 may be in the form of pinch valves, comprising an actuator operable to bias against the flexible tube until the liquid channel inside the tube is in squeezed closed state, or to bias away from the squeezed closed state to allow liquid to flow through the channel in the flexible tube.

It may be noted however that within the scope of the invention other types of valves, per se known in the art of fluid flow systems, such as ball valves, butterfly valves, and disc check valves may be used to open and close the liquid channel.

The chamber portion 22 of the liquid conduit 9 in a fully expanded operational state contains a pump cycle volume of liquid that determines the volume of liquid medicament that may be pumped in each cycle of the dosing unit 6 as will be better described hereinafter.

The chamber portion 22 comprises some elasticity in its expanded operational state, that allows the pump cycle volume to vary as a function of the inlet pressure that is generated by the upstream piston pump 5.

Referring now in particular to FIGS. 4*a* to 4*h* initial pumping steps of the pumping system will now be described.

Starting with FIG. 4*a*, in an initial state when the drug delivery system comprises a new full liquid reservoir 7, the plunger 14 is initially in an uncompressed state.

In a first step, as illustrated in FIG. 4*b* (further considering FIG. 2), the drive 11 is powered to displace the nut 19 and actuation rod 30 in a pumping direction such that the piston plate 32 presses against an outer face of the plunger 14 pushing it into the reservoir container 13 and compressing the liquid contained therein. In this initial compression of the liquid in the reservoir, the inlet valve 24 is closed and prevents liquid flowing therethrough. In an embodiment comprising a pinch valve, the pinch valve actuator pinches the inlet section 18 of the flexible tube 9 such that the liquid channel inside the inlet section is closed.

The inlet valve 24 is then opened as illustrated in FIG. 4c while the plunger 14 is being pressed into the reservoir by the plunger actuator. In an embodiment comprising a pinch valve, the pinch valve actuator biases away from the inlet section 18 of the flexible tube 9 such that the liquid channel inside the inlet section is opened.

Liquid is thus forced into the chamber portion as illustrated in FIG. 4d, either by actively biasing the pump chamber actuator 28 away from the closed position to an expanded position, or by passively allowing the pump chamber actuator 28 to elastically bias away from the closed position to an expanded position due to the pressure of the liquid pumped by the upstream piston pump 5 into the chamber portion 22. In this regard, the pump chamber actuator may comprise an active electrical actuator, or may comprise a spring biased actuator that presses on the chamber portion 22 of the flexible tube.

Figure 5A:
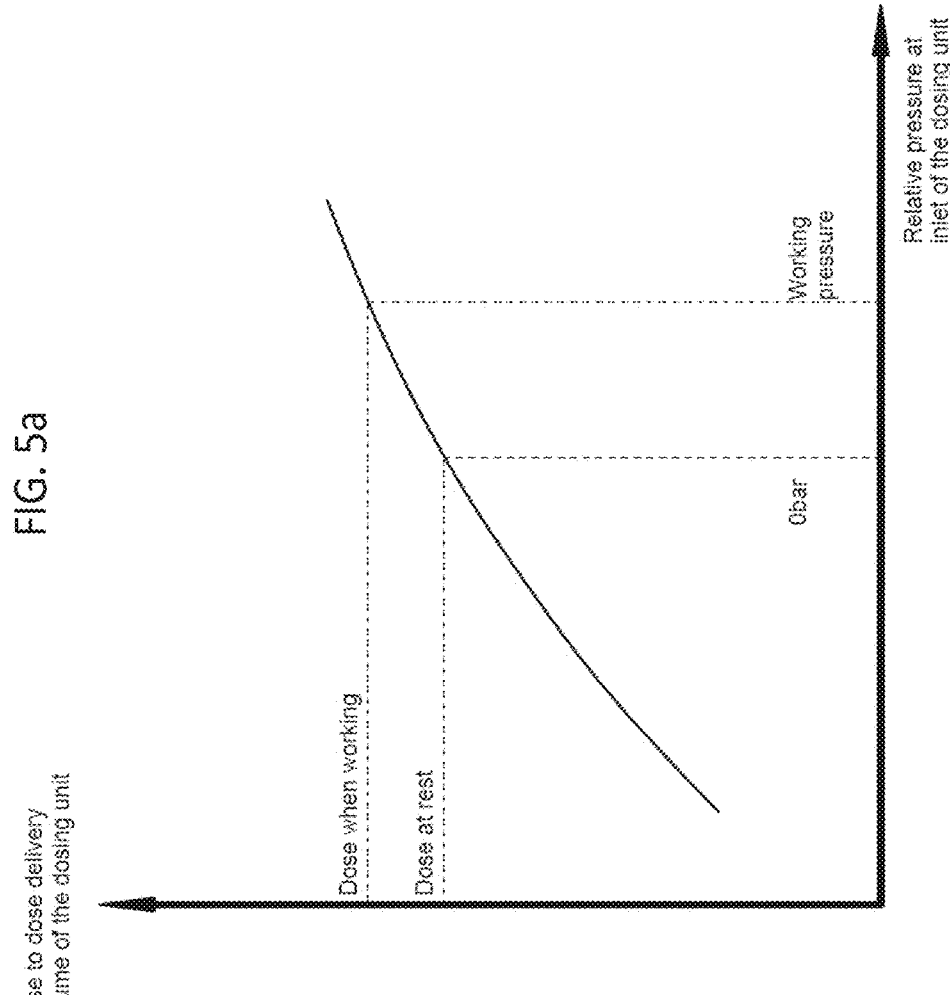
FIGS. 5*a*, 5*b* and 5*c* are graphs illustrating the delivery volume of the pumping system as a function of the relative pressure at the inlet of the dosing unit, according to various embodiments of the invention.

The chamber portion 22 comprises some elasticity in its full state configured to allow the chamber portion 22 in its full state to expand elastically as a function of the pressure that is applied to the liquid. An example of the elastic expansion characteristic of the chamber portion in its full state is illustrated in FIG. 5a, whereby the dosage volume of one pump cycle at ambient pressure (at rest) is less than the dosage volume of one pump cycle at an operational (working) pressure greater than ambient pressure.

Figures 5B, 5C:
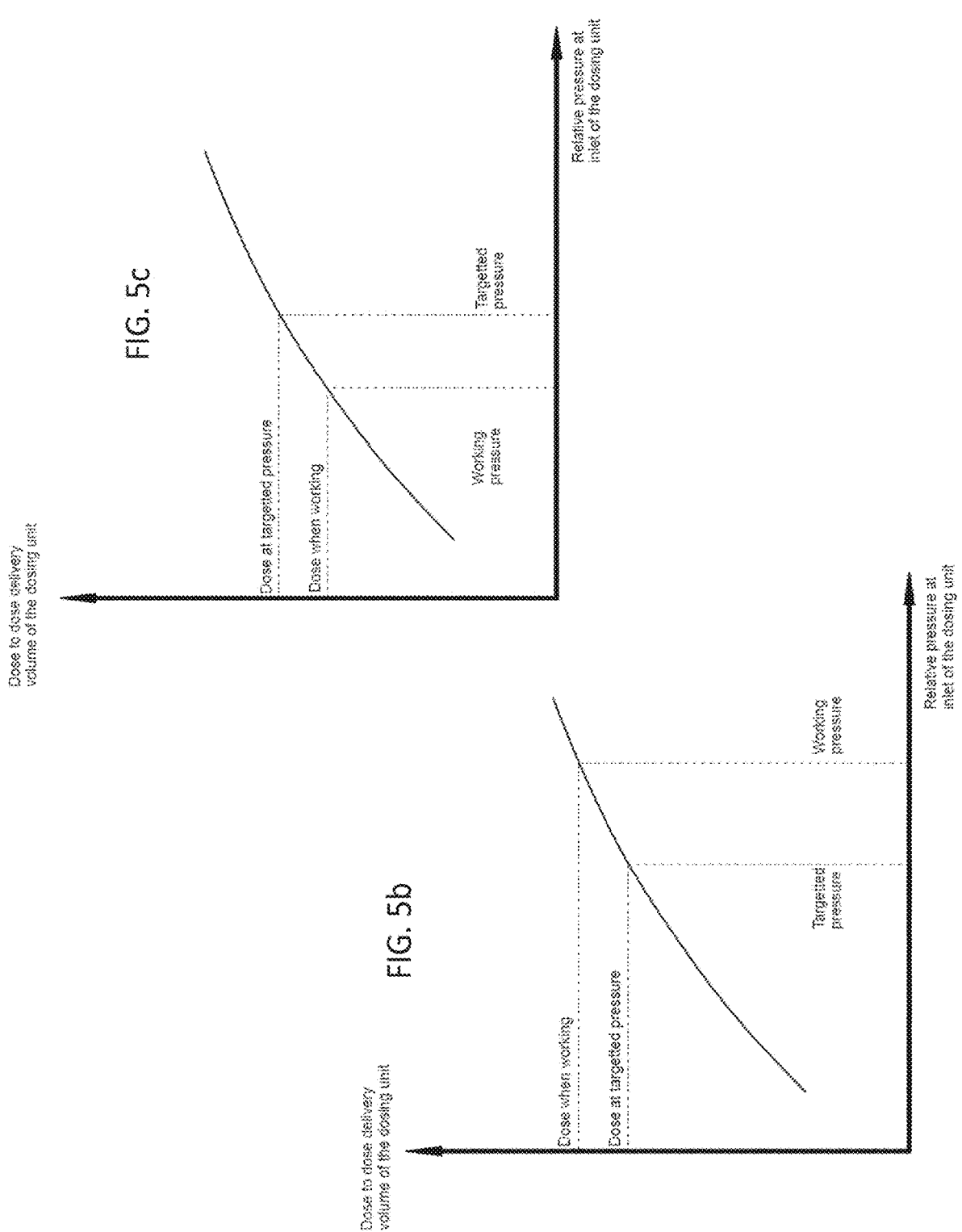

In the embodiment in which the bottom wall 31 is bonded to the base 29 such that the top wall is already under tensile elastic stress when liquid starts being injected in the chamber portion, the elastic expansion characteristic of the chamber portion 22 may have a characteristic as illustrated in FIG. 5b or 5c. In this embodiment, the dosage volume of one pump cycle at a predefined target pressure that is greater than ambient pressure taking into account the compression provided by the wall of the chamber portion, is less or more than the dosage volume of one pump cycle at an operational (working) pressure that determines the dosage per cycle. In other words, the operational (working) pressure may be at a value above the predefined target pressure, or at a value below the predefined target pressure.

In an embodiment comprising a flexible tube forming the liquid conduit, the elasticity may in part or in whole be provided by the material of the flexible tube. In variants however, the elasticity may be provided in whole or in part by a spring biased actuator mounted against, or elastic sleeve mounted around, the chamber portion 22.

Figure 4E:
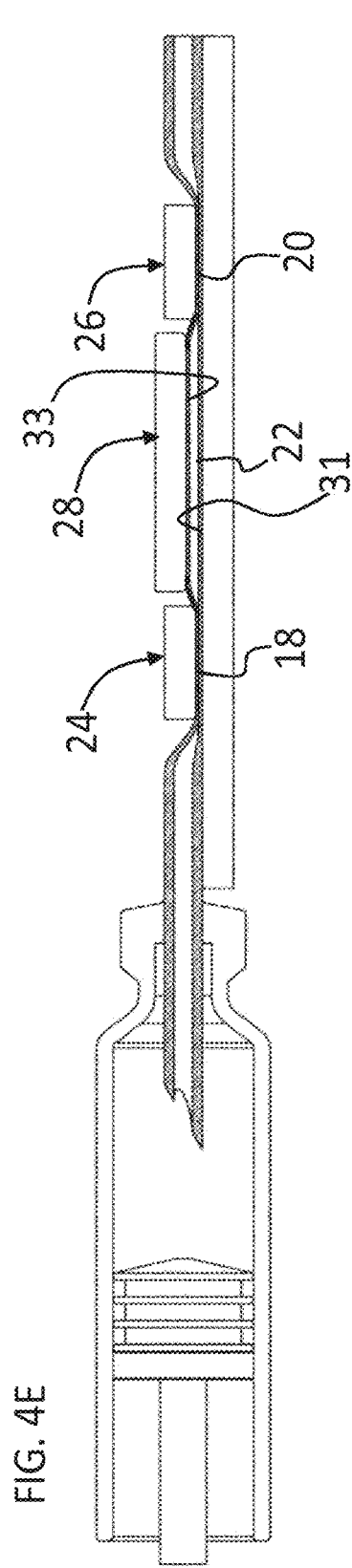
Figure 4F:
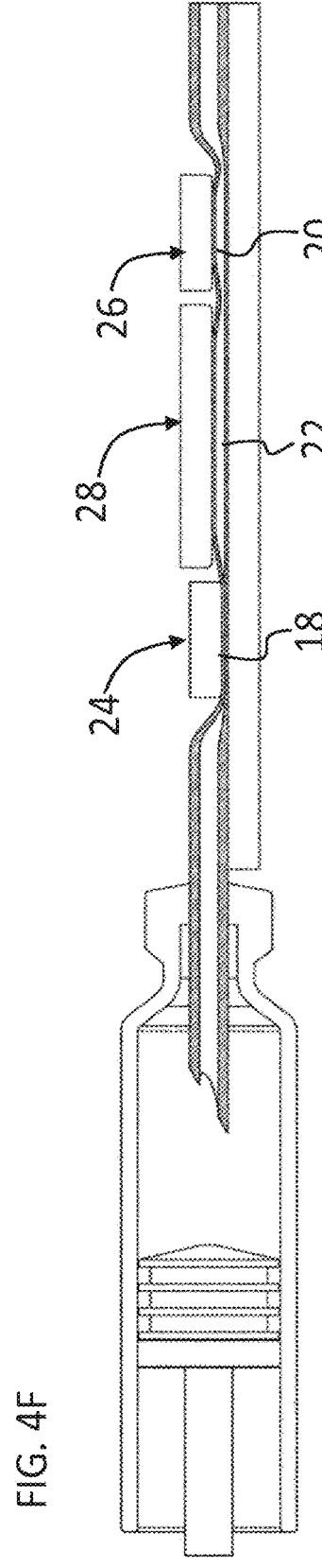

As illustrated in FIG. 4d, liquid goes into the chamber portion 22 and the volume contained therein depends on the pressure in the reservoir 7. In subsequent steps as illustrated in FIG. 4e followed by FIG. 4f, the inlet valve 24 is closed and the outlet valve 26 is opened to allow liquid to flow out through the outlet section 20 of the liquid conduit 9 as illustrated in FIG. 4f thus fluidly connecting the chamber portion 22 to the delivery outlet 12 of the drug delivery device.

Figure 4G:
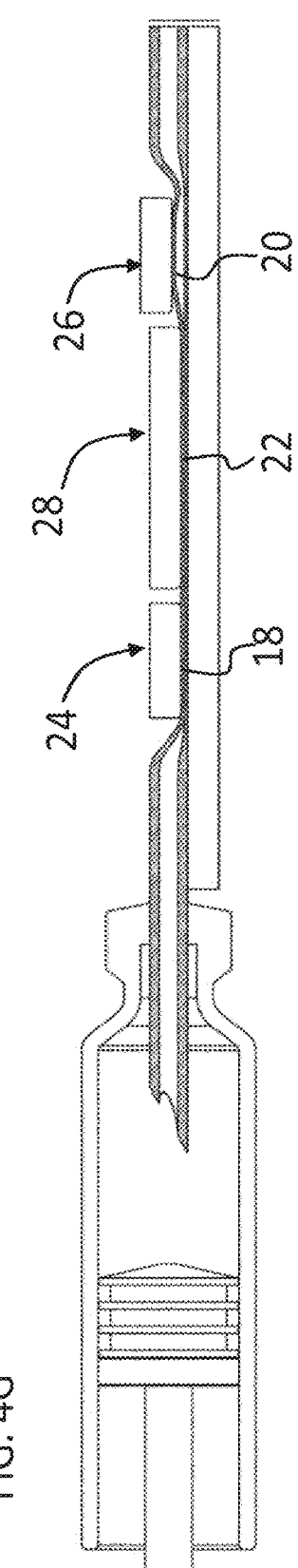
Figure 4H:
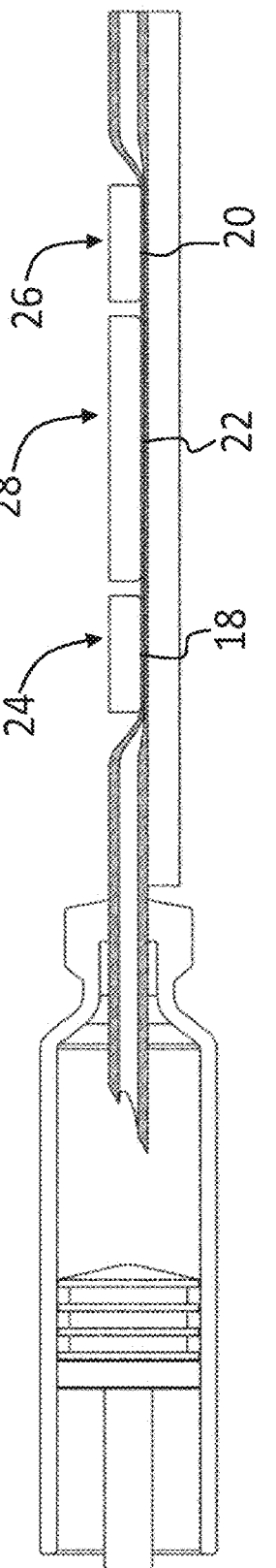

Liquid is ejected from the chamber portion 22, either by applying pressure on the pump chamber actuator 28 by means of an electrically driven actuator or by means of a passive spring biased element applying pressure on the pump chamber actuator 28 until the pump chamber is empty or essentially empty as illustrated in FIG. 4g. The output valve 26 is then closed such that the outlet section 20 of the liquid conduit 9 is closed and a new pump cycle may be started with the steps illustrated in FIGS. 4b to 4h.

It may be noted that the order for carrying out the pumping cycles of the piston pump and the dosing unit can also be reversed or simultaneous. For instance, in a variant, a single motor may be used for actuating both simultaneously.

After the initial pump cycle described above, there is a certain pressure in the liquid reservoir 7 and the plunger 14 is in at least a partially compressed state. It may be noted however that during the first step of opening the inlet section and filling the pump chamber portion 22, due to the stick-slip effect on the elastic plunger 14 the degree of compression of the plunger may vary within a certain range that may lead to the pressure in the reservoir after the first cycle not being completely stabilized within an accurate pre-defined pressure range, for instance within a range of 30% above or below a desired pressure. A second, third, fourth or more cycles of pumping going through the steps illustrated in FIGS. 4b to 4h may be performed in order to ensure that the plunger 14 is compressed within a stabilized range of compression that is independent of the initial uncompressed state. It is also possible in a variant to operate dissimilar numbers of pumping cycles for the piston pump and the dosing unit depending on their respective calibrated pumping volumes.

The first or the first and subsequent second, third, fourth or more initial pumping cycles may constitute an initialization or priming operation for the drug delivery device prior to first use by the patient.

In an embodiment, the initialization procedure may comprise the following steps:

i. the cartridge 7 is inserted and locked into the reusable part 3, whereby the outlet is not yet connected to the disposable part 2, ii. a series of pumping cycles are operated to build a minimal pressure in the cartridge 7, iii. the disposable part 2 is assembled to the reusable part 3 and thus the cartridge 7 is now fluidically connected to the disposable part iv. a few pumping cycles involving both the piston pump 5 and the dosing unit 6 are done in order to fill the system up to the outlet 12 of the disposable part 2, v. the drug delivery device may, according to a variant, be connected to an infusion set.

In an exemplary embodiment, the pressure in the reservoir 7 at the end of a priming operation may be stabilized, for instance in a range of between 200 and 300 millibars, for instance around 250 millibars.

In an advantageous embodiment, the dosing unit is configured such that a minimal number of 100 cycles must be performed for the dosing unit to empty the cartridge. The delivered volume of one cycle is linked to the smallest delivered volume of the drug delivery device.

Advantageously, the overpressure in the liquid reservoir 7 ensures that the pump system delivers accurate volumes of liquid at each cycle with a very low variation of volume from one cycle to the next because of the auto-calibration between the dosing unit 6 and the piston pump 5.

This auto calibration is a consequence of the elasticity of the chamber portion in its expanded operation state compared to the elasticity of the plunger 14, whereby the volume variation of the chamber portion as a function of the pressure variation, is smaller than the volume variation in the liquid reservoir 7 (due to the elasticity of the plunger 14) for the same pressure variation. The dosing unit thus has acts a damping system on possible pressure variations of the liquid reservoir due to the variable position of the elastic plunger subject to a stick slip effect in it's displacement.

Another advantage of the overpressure within the reservoir 7 is the reduction of formation of bubbles due to the increased vapour saturation temperature of the liquid at pressure.

For instance, in the case of insulin, the saturation temperature with 250 millibars of overpressure corresponds, at ambient temperatures, to an increase of about 15° Celsius.

For the sake of completeness, the term "ambient pressure" is considered to be the air pressure in the environment of use of the medical device, which is around 1 bar, and "ambient temperature" is considered to be the ISO standard ambient temperature of 20° C.

In one example for use with concentrated insulin, a volume of liquid injected per cycle corresponds for instance to about 0.5 microliters with 250 millibars pressure (over ambient pressure) delivered by the piston pump, whereas at ambient pressure, namely when the dosing unit 6 functions as a micropump without overpressure at the inlet, the pump cycle volume is about 10% lower, for instance around 0.45 microliters per pump cycle. This last value does not need to be very accurate which is of great advantage for economical high volume production.

In another example for use with concentrated insulin, a volume of liquid injected per cycle corresponds for instance to about 0.25 microliters with 650 millibars pressure (over ambient pressure) delivered by the piston pump, whereas at the target pressure of 750 millibars, the pump cycle volume is about 10% higher, for instance around 0.275 microliters per pump cycle. This last value does not need to be very accurate which is of great advantage for economical high volume production.

With the pressure provided by the piston pump 5 after the priming operation, the dosing unit achieves a stabilized (calibrated) volume of liquid delivered at each cycle that has a very low variation from one cycle to the next. The effects of the variable compression of the plunger 14 due to its elastic properties and the stick-slip effect of friction between the plunger and the reservoir container wall are significantly reduced by the dosing unit 6 because of the stabilized overpressure in the reservoir 7 after each pumping cycle. The overall volume delivered by a plurality of cycles will however depend on the displacement of the plunger 14 by the linear actuator 16 which is very accurate. Thus the drug delivery is accurate both over short and long term use. Moreover, the overpressure provided by the combination of the piston pump and dosing unit reduces the formation of bubbles in the liquid.

In the illustrated embodiments the dosing unit is essentially in the form of a peristaltic pumping unit, in particular a shuttle peristaltic pump however within the scope of the invention, the dosing unit can be in the form of various volumetric incremental pumps with the property that the delivered volume per cycle varies as a function of the inlet pressure. For instance the dosing unit may comprise a membrane type of pump, whereby the elastic membrane of the pump unit has the property that the delivered volume per cycle varies as a function of the inlet pressure. Other membrane, peristaltic or tube pumps with elastic properties may be implemented for the dosing unit.

LIST OF REFERENCES IN THE DRAWINGS

Drug delivery device 1
  reusable part 3
    drive unit 11
      electrical motor 42
      reduction gear mechanism 44
    control system
  disposable part 2
    delivery system outlet 12
    pumping system
      piston pump 5
        liquid reservoir 7
        container wall 13
        plunger 14
        cap 15
        liquid chamber portion
        plunger actuator
        actuation rod 30
        bent portion 30$a$
        straight portion 30$b$
        housing guide slot 34 (in housing)
        piston plate 32
        linear actuator 16
        screw 17
        nut 19
        housing linear guide 38 (for nut)
      dosing unit 6
        peristaltic dosing unit
        connector or needle 36
        flexible tube 9
        inlet 18
        outlet 20
        chamber portion 22
        bottom wall 31
        top wall 33
        actuation system 10
        inlet valve 24
        pinch valve actuator
        outlet valve 26
        pinch valve actuator
        pump chamber actuator(s) 28
        base 29

What is claimed is:

1. A patch pump for pumping liquid from a liquid reservoir to a subject for transcutaneous delivery of the liquid, the patch pump comprising:

a first portion comprising a pump and a first cavity configured to receive a first end of the liquid reservoir, the pump comprising a piston pump comprising a plunger actuator configured to push a plunger into the liquid reservoir at the first end to cause the liquid to be expelled out the liquid reservoir;

a second portion comprising a second cavity configured to receive a second end of the liquid reservoir, the second portion configured to be coupled to the first portion such that the liquid reservoir is held within the first portion and the second portion coupled together, the second portion configured to be separable from the first portion, the second portion comprising a tube configured to be fluidly connected to the liquid reservoir downstream from the liquid reservoir to, responsive to pumping by the piston pump that pushes the plunger into the liquid reservoir at the first end, receive the liquid expelled out of the liquid reservoir for supplying a dose of the liquid transcutaneously to the subject; and a housing support with an adhesive base configured to bond to the subject's skin for supporting the first portion and the second portion coupled together at the subject's skin, wherein the first portion is a reusable portion and the second portion is a disposable portion and further comprising a transcutaneous needle configured to be fixed directly to the disposable portion for transcutaneous delivery of the dose.

2. The patch pump of claim 1, wherein the reusable portion is configured for multi-use and the disposable portion is configured for single-use.

3. The patch pump of claim 1, wherein the housing support is configured to be disposable.

4. The patch pump of claim 1, wherein the liquid is insulin.

5. The patch pump of claim 1, wherein the first portion further comprises a motor configured to drive the piston pump.

6. The patch pump of claim 1, wherein the first portion further comprises a controller configured to control the piston pump.

7. The patch pump of claim 1, wherein the second portion comprises a dosing unit fluidly connected to the tube, the dosing unit configured to generate the dose of the liquid for transcutaneous delivery to the subject.

8. The patch pump of claim 7, wherein the dosing unit comprises a chamber portion configured to receive from the liquid reservoir a discrete pump cycle volume of liquid under an operational pressure generated by the piston pump greater than ambient pressure, and to deliver the pump cycle volume of liquid to a delivery system outlet, the discrete pump cycle volume being dependent on operational pressure.

9. The patch pump of claim 8, wherein the dosing unit comprises a flexible tube incorporating the chamber portion.

10. The patch pump of claim 7, wherein the dosing unit comprises a chamber portion with a top wall and a bottom wall that separate apart as the chamber portion is filled with liquid, wherein the bottom wall is bonded to a base, the bonding arranged along at least portions of a perimeter of the bottom wall such that when liquid is injected into the chamber portion and the top wall moves away from the bottom wall, an elastic tensile stress is generated in the top wall of the chamber portion.

11. The patch pump of claim 7, wherein the dosing unit comprises a plurality of pinch valves configured to move to generate the dose of the liquid with a predefined volume.

12. The patch pump of claim 1, wherein the plunger actuator comprises a curved actuation rod configured to move, responsive to pumping by the piston pump, in a linear manner at a first end of the curved actuation rod, in the linear manner at a second end of the curved actuation rod, and to bend in a mid-section of the curved actuation rod, wherein the movement of the curved actuation rod in the linear manner causes the plunger actuator to push the plunger into the liquid reservoir to cause the liquid to be expelled out the liquid reservoir and into the tube.

13. The patch pump of claim 12, further comprising a motor in the first portion and a reduction gear mechanism between the motor and the curved actuation rod, the motor configured to cause rotation, the reduction gear mechanism configured to cause a reduced rate of rotation compared to the rotation caused by the motor for movement of the curved actuation rod.

14. The patch pump of claim 12, further comprising a motor and a linear actuator, the linear actuator comprising a screw and a nut coupled to the curved actuation rod and slideably movable along the screw upon rotation of the screw responsive to rotation of the motor to cause movement of the curved actuation rod.

15. The patch pump of claim 12, wherein the curved actuation rod comprises a curved spring sheet beam, the actuation rod having a portion bent in a U-shape between straight sections.

16. The patch pump of claim 1, wherein the tube is a needle configured to pierce a cap at the second end of the liquid reservoir.

* * * * *